United States Patent [19]

Bouillon et al.

[11] 4,087,550

[45] May 2, 1978

[54] HYDROXYLATED AMINE THIOETHERS FOR IMPROVING THE GREASY AND UNAESTHETIC APPEARANCE OF THE HAIR AND SKIN

[75] Inventors: Claude Bouillon, Eaubonne; Charles Vayssié, Aulnay-sous-Bois, both of France

[73] Assignee: L'Oreal, Paris, France

[21] Appl. No.: 677,087

[22] Filed: Apr. 15, 1976

Related U.S. Application Data

[62] Division of Ser. No. 401,380, Sep. 27, 1973, Pat. No. 3,968,218.

[30] Foreign Application Priority Data

Sep. 29, 1972 Luxembourg .......................... 66207

[51] Int. Cl.$^2$ .................. A61K 31/165; A61K 31/60; A61K 31/205; A61K 31/455; A61K 31/195; A61K 31/13; A61K 31/135; A61K 31/16

[52] U.S. Cl. ..................................... 424/319; 424/70; 424/71; 424/72; 424/248.52; 424/250; 424/233; 424/266; 424/274; 424/282; 424/316; 424/317; 424/320; 424/324; 424/325; 424/330; 424/318; 544/158; 544/124; 544/148; 544/159; 544/131; 424/DIG. 1; 424/DIG. 2; 424/DIG. 4

[58] Field of Search ............... 424/233, 266, 316, 319, 424/320, 324, 325, 330, DIG. 4, 71, 72, DIG. 2

[56] References Cited

U.S. PATENT DOCUMENTS

| 3,322,635 | 5/1967 | Erkmann et al. .................. 424/70 X |
|---|---|---|
| 3,671,643 | 6/1972 | Kalopissis ............................ 424/319 |
| 3,821,405 | 6/1974 | Kalopissis et al. .................. 424/319 |

*Primary Examiner*—Albert T. Meyers
*Assistant Examiner*—Vera C. Clarke
*Attorney, Agent, or Firm*—Cushman, Darby & Cushman

[57] ABSTRACT

A method and composition for combatting the greasy and unaesthetic appearance of the hair and to improve the appearance of the skin comprises in a carrier at least one active component of the formula $$R-S-CH_2-CH(OH)-CH_2-N(R_1)(R_2)$$

wherein $R_1$ and $R_2$ are methyl, ethyl, isopropyl, cyclohexyl, benzyl or β-hydroxyethyl, or $R_1$ and $R_2$ taken together form $-(CH_2)_2-(CH_2)_2-$, $-(CH_2)_2-CH_2-(CH_2)_2-$, $-(CH_2)_2-O-(CH_2)_2-$, $-(CH_2)_2-N(CH_3)-(CH_2)_2-$, or $-(CH_2)_2-N(C_6H_5)-(CH_2)_2-$;

and R is (i) linear or branched alkyl having 1-18 carbon atoms, (ii) alkenyl having 3-18 carbon atoms, (iii) alkyl having 2-3 carbon atoms and substituted by 1-2 alcohol functions, (iv) $-(CH_2)_m-CH(OR_3)_2$ wherein $R_3$ is alkyl having 1-4 carbon atoms and $m$ is 1-2, (v) $-(CH_2)_nR_4$ wherein $n$ is 0, 1 or 2 and $R_4$ is 2-pyridyl or phenyl, (vi) $-(CH_2)_qR'_4$ wherein $q$ is 0 or 1 and $R'_4$ is 1-naphthyl, 2-naphthyl or [phenyl ring with $(R_5)_p$ substituent]

wherein $p$ is 1, 2 or 3 in which instance $R_5$ is F, Cl, Br, alkoxy having 1-5 carbon atoms or alkyl having 1-4 carbon atoms, or wherein $p$ is 1 in which instance $R_5$ is amino, dimethylamino and methylenedioxy, (vii) $-CH(C_6H_5)_2$, (viii) $-C(C_6H_5)_3$, (ix) $-CH(C_6H_4-p-OCH_3)_2$, (x) $-CH_2-CH(NH_2)-COOH$ (xi) $-CH_2-CH_2-NH-Y$ wherein Y is hydrogen, nicotinyl or $COR_9$ wherein $R_9$ is hydrogen, alkyl having 1-18 carbon atoms, alkenyl having 2-18 carbon atoms or [phenyl ring with $R_{11}$ substituent]

wherein $R_{11}$ is H, F, Cl, Br or alkoxy having 1-4 carbon atoms, (xii) $-CH(COOH)-CH_2-COOH$, and (xiii) $-(CH_2)_s-COOH$ wherein $s$ is 1-10.

12 Claims, No Drawings

HYDROXYLATED AMINE THIOETHERS FOR IMPROVING THE GREASY AND UNAESTHETIC APPEARANCE OF THE HAIR AND SKIN

This is a division, of application Ser. No. 401,380 filed Sept. 27, 1973, now U.S. Pat. No. 3,968,218.

The present invention relates to cosmetic compositions which when administered orally or topically to a human being having hair, skin or scalp characterized by a greasy and unaesthetic appearance significantly improves the condition and appearance of the hair, scalp and skin by essentially eliminating this greasy and unaesthetic appearance. This condition of a greasy and unaesthetic appearance of the hair, skin and scalp can be occasioned by excessive secretions of the sebaceous glands and the compositions of this invention are useful in diminishing such excessive secretions. The compositions are also useful to combat dandruff.

It has already been proposed for use in combatting against the greasy appearance of the hair as well as against the unaesthetic appearance of the skin certain S-substituted derivatives of cysteine and cysteamine.

However, after further investigation, it has now been found that by using as the active component a hydroxylated amino thioether, an activity greater than that of previously known compounds for combatting against a greasy and unaesthetic appearance of the hair and skin is achieved.

Moreover, it has been established that these hydroxylated amino thioethers exhibit excellent solubility in water and hydro-alcoholic solutions, a characteristic which permits the realization of many different types of cosmetic formulations. This solubility feature is due in particular to the presence of a hydroxyl group in the molecule of these active compounds.

Consequently, relative to the previously known compounds, the active compounds of the present invention, exhibit increased activity and better solubility in water, alcohol and hydroalcoholic solutions.

The present invention has for an object a new composition for combatting against the greasy and unaesthetic appearance of the hair and to improve the appearance of the skin, characterized by the fact that it contains in combination in an appropriate carrier, at least one active compound of the formula

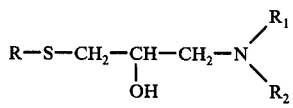
(I)

wherein:

$R_1$ and $R_2$ each independently, are selected from the group consisting of methyl, ethyl, isopropyl, cyclohexyl, benzyl and B-hydroxyethyl, or $R_1$ and $R_2$ taken together form a divalent radical selected from the group consisting of $-(CH_2)_2-(CH_2)_2-$, $-(CH_2)_2-CH_2-(CH_2)_2-$, $-(CH_2)_2-O-(CH_2)_2-$,

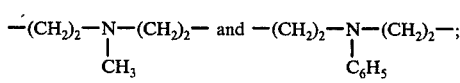

and
R is selected from the group consisting of:

(i) linear or branched alkyl having 1–18 carbon atoms,
(ii) alkenyl having 3–18 carbon atoms,
(iii) alkyl having 2–3 carbon atoms and substituted by 1–2 alcohol functions, i.e., OH groups,
(iv) $-(CH_2)_m-CH(OR_3)_2$ wherein $R_3$ is alkyl having 1–4 carbon atoms and $m$ is 1–2,
(v) $-(CH_2)_nR_4$ wherein $n$ is 0, 1 or 2 and $R_4$ is selected from the group consisting of 2-pyridyl and phenyl,
(vi) $-(CH_2)_qR'_4$ wherein $q$ is 0 or 1 and $R'_4$ is selected from the group consisting of 1-naphthyl, 2-naphthyl and

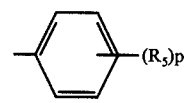

wherein $p$ is 1, 2 or 3 in which instance $R_5$ is selected from the group consisting of F, Cl, Br, alkoxy having 1–5 carbon atoms and alkyl having 1–4 carbon atoms, or wherein $p$ is 1 in which instance $R_5$ is selected from the group consisting of amino, dimethylamino and methylenedioxy, (vii) $-CH(C_6H_5)_2$,
(viii) $-C(C_6H_5)_3$,
(ix) $-CH(C_6H_4p-OCH_3)_2$,

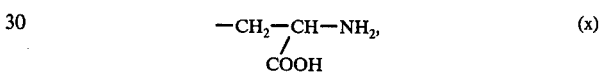
(x)

(xi) $-CH_2-CH_2-NH-Y$ wherein Y is selected from the group consisting of hydrogen, nicotinyl and $COR_9$ wherein $R_9$ is selected from the group consisting of hydrogen, alkyl having 1–18 carbon atoms, alkenyl having 2–18 carbon atoms and

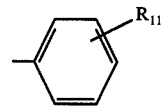

wherein $R_{11}$ is selected from the group consisting of H, F, Cl, Br and alkoxy having 1–4 carbon atoms,

(xii)

and
(xiii) $-(CH_2)_s-COOH$ wherein $s$ is 1–10.

In one preferred embodiment of the present invention, the active compound has the formula

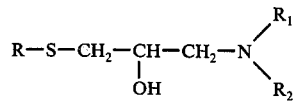

wherein $R_1$ and $R_2$ have the meanings given above and R is selected from the group consisting of
(i) $-(CH_2)_s-COOH$ wherein $s$ is 1–10, $$-CH_2-CH-COOH \text{ and} \atop NH_2$$
(ii)

-continued

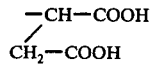 (iii)

In another preferred embodiment the active compound has the formula

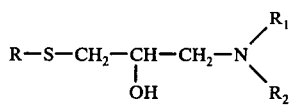

wherein $R_1$ and $R_2$ have the meanings given above and R is selected from the group consisting of
(i) alkyl having 1–18 carbon atoms,
(ii) alkenyl having 3–18 carbon atoms,
(iii) alkyl having 2–3 carbon atoms and substituted by 1–2 OH groups,

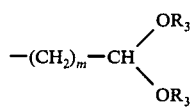 (iv)

wherein $R_3$ is alkyl having 1–4 carbon atoms and $m$ is 1–2, and
(v) $-CH_2-CH_2-NH-Y$ wherein Y has the meaning given above.

In yet another preferred embodiment the active compound has the formula

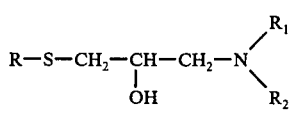

wherein $R_1$ and $R_2$ have the meanings given above and R is selected from the group consisting of:

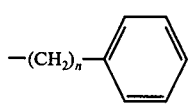 (i)

wherein $n$ is 0, 1 or 2,
(ii) $-(CH_2)_q-R'_4$ wherein $q$ and $R'_4$ have the meanings given above,
(iii) $-CH(C_6H_5)_2$
(iv) $-C(C_6H_5)_3$ and
(v) $-CH(C_6H_4p-OCH_3)_2$ The active compounds of the present invention can be employed either in the form of a free base or in the form of a salt of a mineral or organic acid.

Among the different acids which can be used to obtain these salts, one can particularly mention, without being limited thereto:
mineral acids such as HCl, HBr, sulfuric acid or phosphoric acid, and
organic acids such as malic acid, citric acid, 3-hydroxy butyric acid, lactic acid, gluconic acid, isethionic acid, salicyclic acid, glutamic acid, aspartic acid, camphocarbonic acid, camphosulfonic acid, tartaric acid and nicotinic acid.

Representative compounds that can be used in the compositions of the present invention include the following:
(1) 1-(3-dodecylthio-2-hydroxy propyl) piperidine hydrochloride,
(2) (2-hydroxy-3-octadecylthio propyl) dimethylamine hydrochloride,
(3) 1-(2-hydroxy-3-methylthio propyl)-pyrrodidine hydrochloride,
(4) 4-(3-decylthio-2-hydroxy propyl) morpholinium tartrate,
(5) 1-(3-decylthio-2-hydroxy propyl)-4-methyl piperazine dihydrochloride,
(6) 1-(2-hydroxy-3-octylthio propyl) piperidinium malate,
(7) (3-hexadecylthio-2-hydroxy propyl) bis ($\beta$-hydroxyethyl) amine hydrochloride,
(8) [2-hydroxy-3-(octadecene-9-yl thio) propyl] dicyclohexylamine hydrochloride,
(9) [2-hydroxy-3-(undecene-10-yl thio) propyl] morpholino hydrochloride,
(10) [3-(butene-2-yl thio)-2-hydroxy propyl] diethylamine hydrochloride,
(11) 1-(2-hydroxy-3-$\beta$-hydroxyethylthio propyl) pyrrolidine hydrochloride,
(12) 1-[3-(2,3-dihydroxy propylthio)-2-hydroxy propyl] piperidinium camphosulfonate,
(13) 4-[3-(2,3-dihydroxy propylthio)-2-hydroxy propyl] morpholinium nicotinate,
(14) N-[3-(2,3-dihydroxy-propylthio)-2-hydroxy propyl] N'-methyl piperazinium malate,
(15) [3-(2,3-dihydroxy-propylthio)-2-hydroxy propyl] diethylamine hydrochloride,
(16) [3-(2,2-dimethoxy ethylthio)-2-hydroxy propyl] dimethylamine hydrochloride,
(17) 4-[3-(3,3-dimethoxy propylthio)-2-hydroxy propyl] morpholine,
(18) [2-hydroxy-3-(2-pyridyl thio) propyl] dimethylamine dihydrochloride,
(19) [2-hydroxy-3-(2-pyridyl ethylthio) propyl] diethylamine dihydrochloride,
(20) 1-[2-hydroxy-3-(2-pyridyl thio) propyl] pyrrolidine dihydrochloride,
(21) N-(3-benzylthio-2-hydroxy propyl) N'-phenylpiperazinium tartrate,
(22) (3-benzylthio-2-hydroxy propyl) diisopropylamine hydrochloride,
(23) N-(3-benzylthio-2-hydroxy propyl) morpholine hydrochloride,
(24) N-(3-benzylthio-2-hydroxy propyl) pyrrolidinium glutamate,
(25) (3-benzylthio-2-hydroxy propyl) bis (2-hydroxy ethyl) amine hydrochloride,
(26) N-(3-benzylthio-2-hydroxy propyl) piperidine hydrochloride,
(27) (3-benzylthio-2-hydroxy propyl) diethylamine hydrochloride,
(28) (3-decylthio-2-hydroxy propyl) methyl benzylamine hydrochloride,
(29) (3-p-chlorobenzylthio-2-hydroxy propyl) diethylamine hydrochloride,
(30) N-(3-o-chlorobenzylthio-2-hydroxy propyl) pyrrolidine hydrochloride,
(31) 4-(3-o-fluorophenylthio-2-hydroxy propyl) morpholine,
(32) 1-(3-o-chlorobenzylthio-2-hydroxy propyl) piperidine,

(33) 1-(3-p-fluorobenzylthio-2-hydroxy propyl)-4-methyl piperazine,
(34) (3-m-fluorobenzylthio-2-hydroxy propyl) dimethylamine hydrochloride,
(35) (3-p-bromophenylthio-2-hydroxy propyl) diethylamine hydrochloride,
(36) [3-(2,4-dichloro benzylthio)-2-hydroxy propyl] diethylamine,
(37) [3-(3,4-dichloro benzylthio)-2-hydroxy propyl] piperidine,
(38) (2-hydroxy-3-p-methoxybenzylthio propyl) diisopropylamine hydrobromide,
(39) [3-(p-butoxybenzylthio)-2-hydroxy propyl] bis (2-hydroxy ethyl) amine,
(40) [2-hydroxy-3-(o-methylbenzylthio) propyl] diethylamine,
(41) N-[3-(3,4-dimethoxy benzylthio)-2-hydroxy propyl] piperidine hydrochloride,
(42) 1-(2-hydroxy-3-phenylthio propyl) morpholine hydrochloride,
(43) (2-hydroxy-3-phenylthio propyl) dicyclohexylamine,
(44) (2-hydroxy-3-phenylthio propyl) bis (2-hydroxy ethyl) amine hydrochloride,
(45) 1-(2-hydroxy-3-phenylthio propyl) piperidine hydrochloride,
(46) N-(3-p-aminophenylthio-2-hydroxy propyl) pyrrolidine,
(47) N-(3-p-dimethylamino phenylthio-2-hydroxy propyl) piperidine,
(48) N-(2-hydroxy-3-piperonylthio propyl) morpholine hydrochloride,
(49) (3-o-amino-phenylthio-2-hydroxy propyl) diethylamine,
(50) N-(3-o-aminophenylthio-2-hydroxy propyl) morpholine hydrochloride,
(51) N-(3-benzhydrylthio-2-hydroxy propyl) morpholine,
(52) (2-hydroxy-3-$\alpha$-phenethylthio propyl) diethylamine,
(53) 3-(2-hydroxy-3-morpholino propylthio) alanine,
(54) N-(3-$\beta$-aminoethylthio-2-hydroxy propyl) N'-phenyl piperazine,
(55) [2-hydroxy-3-(2-chlorobenzamido ethylthio) propyl] diethylamine,
(56) N-[2-hydroxy-3-(2-nicotinamido ethylthio) propyl] piperidine,
(57) N-[2-hydroxy-3-(2-dodecanamido ethylthio) propyl] piperidine dihydrochloride,
(58) N-[2-hydroxy-3-(2-o-methoxylbenzamido ethylthio) propyl] piperidine,
(59) N-[2-hydroxy-3-(2-phenylacetamido ethylthio) propyl] piperidine,
(60) N-[2-hydroxy-3-(10-undecene-2-amido ethylthio) propyl] morpholine,
(61) 5-hydroxy-6-piperidino-3-thia hexanoic acid,
(62) 5-hydroxy-6-pyrrolidino-3-thia-hexanoic acid,
(63) 5-hydroxy-6-morpholino-3-thia-hexanoic acid,
(64) 11-(2-hydroxy-3-morpholino propylthio) undecanoic acid,
(65) 5-hydroxy bis-6-(hydroxyethylamino)-3-thia hexanoic acid,
(66) 5-hydroxy-6-(4-methyl piperazino)-3-thia hexanoic acid,
(67) 3-(2-hydroxy-3-piperidino propylthio) propanoic acid,
(68) 5-hydroxy-6-(N-methylbenzylamino)-3-thia hexanoic acid,
(69) 6-dicyclohexylamino-5-hydroxy-3-thia hexanoic acid,
(70) 6-diethylamino-5-hydroxy-3-thia hexanoic acid,
(71) N-(3-decylthio-2-hydroxy propyl) piperidine hydrochloride,
(72) N-[3-(2-m-fluorobenzamido ethylthio)-2-hydroxy propyl] piperidine,
(73) [2-hydroxy-3-(2-tetradecanamido ethyl thio) propyl] diethylamine hydrochloride,
(74) [2-hydroxy-3-(2-hexadecanamido ethylthio) propyl] diethylamine hydrochloride,
(75) N-(2-hydroxy-3-octylthio-propyl) piperidine hydrochloride,
(76) N-(2-hydroxy-3-octadecylthio propyl) piperidine hydrochloride,
(77) N-(2-hydroxy-3-phenylthio propyl) N'-methyl piperazine dihydrochloride,
(78) N-(3-benzylthio-2-hydroxy-propyl) N'-methyl piperazine dihydrochloride and
(79) N-(2-hydroxy-3-$\beta$-hydroxyethylthio propyl) piperidine hydrochloride.

The new compositions of the present invention can be provided in a variety of forms and they contain from 0.5 to 20, and preferably from 1 to 10 percent by weight of at least one active compound of formula I as defined above.

Thus, the compositions can be aqueous or hydroalcoholic solutions or suspensions and comprise lotions for the care of the scalp.

The low molecular weight alcohols which are generally used to produce the hydroalcoholic solutions or suspensions are ethanol and isopropanol.

The compositions of the present invention can contain the above defined active compounds either singly, or as mixtures thereof, or even in admixture with other compounds previously known for use in combatting against a greasy and unaesthetic appearance of hair, or even in admixture with bactericide or fungicides.

The compositions of the present invention can also contain such components as penetrating agents or perfumes which are generally employed in cosmetic preparations.

The present invention also has for an object a process for treating hair in order to improve its appearance, said process being essentially characterized by the fact that the composition defined above is applied with massaging onto the scalp or hair. The quantity applied is generally between 10—20 cc of said composition.

The new cosmetic compositions of the present invention can also take the form of a hair setting lacquer or lotion containing at least one active compound as defined in formula I in an appropriate cosmetic vehicle, or carrier with at least one conventional cosmetic film forming resin, generally having a molecular weight ranging from about 10,000 – 70,000.

Representative cosmetic resins that can be employed include polyvinylpyrrolidone having a molecular weight ranging from 10,000 – 70,000; copolymer of vinylpyrrolidone and vinyl acetate (70%:30% to 30%: 70%-K ethanol 1% 25–50); copolymer of vinyl acetate and an unsaturated carboxylic acid such as crotonic acid (90%/10% molecular weight — 20,000); copolymer resulting from the polymerization of vinyl acetate (75–85%), crotonic acid (5–15%) and an acrylic or methacrylic ester or an alkyl vinyl either (5–15%); copolymer resulting from the copolymerization of vinyl acetate (63–88%), crotonic acid (5–15%) and a vinyl ester of long carbon chain acid having 10–22 carbon atoms or even an allyl or methallyl ester of a long carbon chain acid having 10–22 carbon atoms (5–25%); copolymer resulting from the copolymerization of an ester of an unsaturated alcohol having 2–12 carbon atoms and a saturated short carbon chain carboxylic acid having 2–5 carbon atoms (65–80%) and unsaturated short carbon chain acid having 4–20 carbon atoms (7–12%) and at least one ester of a saturated long carbon chain alcohol having 8–18 carbon atoms and an unsaturated short carbon chain acid having 4–20 carbon atoms (10–20%); and a copolymer resulting from the polymerization of at least one unsaturated ester and at least one unsaturated acid.

In a particular embodiment of the invention, the cosmetic resins contained in the compositions can have lateral side chains at the extremity of which can be found a thiol function.

The cosmetic resins contained in these compositions in the form of a hair setting lotion or lacquer can also be constituted by colored polymers, that is, polymers containing in the macromolecular chains dye molecules which impart to the hair a particular coloration or shade.

These compositions can also contain direct dyes to effect coloring or tinting of the hair.

The compositions can also contain components conventionally employed in cosmetic preparations for setting the hair such as penetrating agents, surfactants, dyes, perfumes and the like.

The cosmetic vehicle or carrier used to produce this type of composition can be constituted by mixtures conventionally used to produce hair setting lacquers or lotions.

Thus, these cosmetic compositions can comprise an alcoholic or hydroalcoholic solution of at least one active compound of formula I and of a resin to provide a hair setting lotion. A hair setting lotion can be, for example, provided by introducing into a hydroalcoholic solution having a content of 0–70% alcohol, 1–20% and preferably 1–3% relative to the solution of a resin as defined above.

The alcoholic or hydroalcoholic solution of the active compound can also be mixed with a conventional quantity of liquified propellant gas under pressure and packaged in an aerosol container and constitute that which is conventionally considered a lacquer for the hair.

For example, an aerosol lacquer for the hair can be provided by introducing 1–20%, preferably 1–5%, of a resin as defined above in a mixture comprising ¼ to ½ by weight of a lower alkanol and ⅔ to ¾ by weight of a liquified propellant gas under pressure. Conventional aerosol propellants such as fluorinated hydrocarbons including the Freons can be employed. Representative of such propellants are dichlorodifluoromethane, trichloromonofluoromethane and mixtures thereof. Obviously, other well known propellants can also be used.

In these hair setting lotions or lacquers, the concentration of the active compound is generally from 0.5 to 20 weight percent, thereby making it possible to treat the hair by subjecting it to a hair setting operation, this process being essentially characterized by the fact that the hair is impregnated with said composition containing in combination the active compound of formula I with a conventional cosmetic resin, rolling the hair up on hair setting rollers and drying the hair.

The cosmetic compositions of this invention can also take the form of a topically applied shampoo which also effectively combats against a greasy and unaesthetic appearance of the hair.

These shampoo compositions are essentially characterized by the fact that they contain, in combination, at least one anionic, cationic, nonionic or amphoteric detergent with at least one active compound of formula I as defined above.

Representative anionic detergents include alkyl sulfates, alkylether sulfates, alkylpolyether sulfates, alkyl sulfonates (the alkyl moiety having 8–18 carbon atoms), monoglyceride sulfates, alkanolamide sulfates, alkanolamide sulfones, soaps of fatty acids, monosulfosuccinates of fatty alcohols, the condensation product of a fatty acid with isethionic acid, the condensation product of fatty acids with methyl taurine, the condensation product of fatty acids with sarcosine and the condensation product of fatty acids with a protein hydrolyzate.

Representative cationic detergents include long chain quaternary ammoniums, esters of fatty acids and amino alcohols and polyether amines. Specifically, there can be used dilauryldimethyl ammonium chloride, diisobutyl phenoxyethoxy ethyl dimethylbenzyl ammonium chloride, cetyl trimethyl ammonium bromide, N-cetyl pyridinium bromide and benzethonium chloride, lauryl benzyl trimethyl ammonium bromide or chloride, myristyl benzyl trimethyl ammonium bromide or chloride and cetyl benzyl trimethyl ammonium bromide or chloride.

Representative nonionic detergents are the esters of polyols and sugars, the condensation product of ethylene oxide on fatty acids, on fatty alcohols, on long chain alkylphenols, on long chain mercaptans, on long chain amides, and polyethers of polyhydroxylated fatty alcohols.

Suitable amphoteric detergents include asparagine derivatives, the condensation product of monochloroacetic acid on imidazolines and alkylamino propionates.

The shampoo compositions of the present invention contain from 0.1–20%, preferably from 0.5–10% by weight of the active compound of formula I defined above. They also contain, for example, from 4 to 15%, preferably from 5 to 7% by weight of detergent in an aqueous medium and can have a pH of about 3–8.

The shampoos as defined above can also contain other conventional cosmetic components such as perfumes, dyes, or again, bactericides or fungicides especially when the shampoos also have an anti-dandruff activity. They can also contain thickeners such as alkanolamides of fatty acids, cellulose derivatives (for example, carboxymethyl cellulose and hydroxymethyl cellulose), esters of long chain polyols and natural gums, so as to provide a cream or gel.

These shampoo compositions can also be provided in the form of a powder which can be applied either to wet hair, or which can be dissolved in a predetermined volume of water before washing the hair.

These shampoo compositions can also include conventional dyes to tint or color the hair.

The shampoo compositions make it possible to combat against a greasy and unaesthetic appearance of the hair, as well as against dandruff by applying the same to the hair, which optionally can be previously wetted, in amounts effective to impregnate the hair, massaging the scalp for a time in the order of a few minutes and rinsing the hair.

Usually, satisfactory results are obtained by shampooing once a week. This regimen provides a significant reduction and in certain cases, substantially complete elimination of the greasy appearance of the hair, while also providing normal care for the hair.

The cosmetic compositions of this invention can also take the form of a topically applicable composition to effect a permanent waving of the hair exhibiting a greasy or unaesthetic appearance caused by a dandruff condition or an excessive secretion of sebum by the sebaceous glands.

As is known, the permanent deformation of the hair can be achieved in one stage or two stages.

When the permanent deformation of the hair is achieved in two stages, the active compound of formula I above can be present either in the reducing composition employed to effect the first stage, or in the oxidation or neutralization composition employed to effect the second stage of the permanent waving operation.

When the permanent deformation of the hair is achieved in a single stage, a self-neutralizing composition contains, in combination with the self-neutralizing agent, the active compound of formula I above.

In accordance with the invention, the composition for effecting the first stage of a two-stage operation contains at least one compound for reducing the disulfide linkages of keratin, such as thioglycolic acid, ammonium thioglycolate, thioglycerol or thiolactic acid, in combination with at least one active compound of formula I above, present in amounts of 0.1 – 20 weight percent, the pH of the composition being preferably between 3 and 9.5.

The second stage of the operation is then carried out using a conventional oxidizing or neutralizing composition, not containing the active compound of formula I above.

In another embodiment of the present invention the first stage of the permanent wave operation can be carried out using a conventional reducing agent, followed by carrying out the second stage using a neutralizing or oxidizing agent composition containing the active compound of formula I present in an amount between 0.5 – 20% by weight of the composition and preferably between 1-10 weight percent thereof.

When the permanent deformation of the hair is achieved in a single stage, the self-neutralizing composition contains, in combination, a thiol and an organic disulfide in a molar ratio of disulfide to thiol greater than 1, with the active compound of formula I, being present in an amount between 0.1 and 20%, and preferably between 0.5 and 10%, by weight of said composition.

The present invention has also for an object the provision of a composition to effect the permanent deformation of hair such as described above, which composition is packaged in two parts.

According to this embodiment of the invention, one part can be constituted by a conventional reducing composition, while the other part can contain the active compound of formula I or, alternatively, one part is constituted by a conventional neutralizing composition while the other part is constituted by the active compound of formula I.

The composition of this invention employed to effect a permanent deformation of the hair can also contain conventional components for similar cosmetic compositions such as penetrating agents, surface active agents, dyes and perfumes.

The cosmetic vehicle or carrier useful for the production of these permanent waving compositions can be those generally employed for the production of permanent waving compositions such as water, lower alkanols and their mixtures as defined above. Further, these compositions can be provided in the form of a solution, foam, cream or gel.

In a particular embodiment, the alcoholic or hydroalcoholic solution employed as the carrier in the permanent waving composition can also be used in combination with a conventional quantity of liquified propellant gas and packaged under pressure in an aerosol container to provide a sprayable aerosol formulation.

These permanent waving compositions make it possible to perform a process for effecting the permanent waving of greasy hair, in two steps or in a single stage operation, this process being characterized by the fact that the reducing or neutralization composition, or the self-neutralization composition contains, in addition to the reducing or oxidizing agent, or conventional self-neutralizer, at least one active compound of formula I above.

In yet another embodiment of the present invention a dermal lotion can be prepared which contains the active compound defined above in combination with an appropriate cosmetic vehicle for application to the skin to improve its appearance when it exhibits a greasy appearance. Such compositions can, preferably, be provided in the form of a cream, milk, gel, dermatological cake or aerosol foam. These compositions can also be provided as an aqueous or hydroalcoholic solution.

Such dermal lotions generally contain between 0.5-20 weight percent of at least one active compound according to formula I above. These compositions can also contain any conventional component usually employed in facial beauty creams, such as fatty bodies, emulsifiers, preservatives, perfumes, dyes and waxes. They can also contain colored pigments which permit to color the skin and mask skin defects.

These compositions which can be applied to the skin also make it possible to perform a process for improving the appearance of the skin, this process being characterized by the fact that a composition as defined above is applied to those parts of the skin requiring treatment.

These dermal compositions can also contain bactericides or fungicides. As has been stated before, the use of such agents is particularly recommended in compositions for use in combatting dandruff as well as in dermal lotions to improve the appearance of oily skin.

Representative bactericides or fungicides useful in the present invention include hexachlorophene, quaternary ammonium compounds such as tetradecyltrimethyl ammonium bromide as well as compounds described in Luxembourg Pat. Nos. 59,405; 60,384 and 65,350.

In accordance with another embodiment of the invention there is provided a composition and method for eliminating or significantly reducing a greasy and unaesthetic appearance of the hair and scalp which comprises orally administering to a human being having hair and a scalp so characterized a therapeutic composition comprising an ingestible carrier admixed with, as a non-toxic active component, the active compound of formula I.

In the case of greasy appearing hair which can, as stated above, be caused by an excessive secretion of sebum by the sebaceous glands, such treatment is particularly advantageous in that the greasy appearance can be eliminated without disturbing the coiffure.

The oral composition of this invention generally contains the active compound in amounts between 0.1-50% and, preferably, between 1–20% by weight of said composition.

The active compound can be dissolved in an alimentary liquid, such as water or an aqueous solution of a non-toxic lower alcohol, optionally aromatized.

The active compound can also be incorporated into a solid ingestible excipient and be present, for example, in the form of granules, pills, tablets or lozenges. They can also be dissolved in an alimentary liquid which in turn is packaged in an ingestible capsule.

The active compounds of the present invention are non-toxic and, therefore, the specific amounts orally administered can be left to the discretion of the user. However, it has been found appropriate to use the orally administered compositions for successive periods of 15 days with a 15 day interruption at a dosage of about 100 mg. per 24 hour period.

These oral compositions make it possible to carry out a process for combatting against a greasy and unaesthetic appearance of the hair and skin, this process being characterized by the fact that a composition containing the active compound, in combination with an ingestible vehicle is orally administered to a person having hair and skin so characterized.

The present invention also relates to the following new compounds:

(1) 1-(3-dodecylthio-2-hydroxy propyl) piperidine hydrochloride,
(2) (2-hydroxy-3-octadecylthio propyl) dimethylamine hydrochloride,
(3) 1-(2-hydroxy-3-methylthio propyl) pyrrolidone hydrochloride,
(4) 4-(3-decylthio-2-hydroxy propyl) morpholinium tartrate,
(5) m-(3-decylthio-2-hydroxy propyl) piperazine dihydrochloride,
(6) 1-(2-hydroxy-3-octylthio propyl) piperidinium malate,
(7) (3-hexadecylthio-2-hydroxy propyl) bis ($\beta$-hydroxyethyl) amine hydrochloride,
(8) [2-hydroxy-3-(octadecen-9-yl thio) propyl] dicyclohexylamine hydrochloride,
(9) [2-hydroxy-3-(undecene-10-ylthio) propyl] morpholine hydrochloride,
(10) [3-(butene-2-ylthio)-2-hydroxy propyl] diethylamine hydrochloride,
(11) 1-(2-hydroxy-3-$\beta$-hydroxyethylthio propyl) pyrrolidine hydrochloride,
(12) 1-[3-(2,3-dihydroxy propylthio)-2-hydroxy propyl] piperidinium camphosulfonate,
(13) 4-[3-(2,3-dihydroxy propylthio)-2-hydroxy propyl] morpholinium nicotinate,
(14) N-[3-(2,3-dihydroxy propylthio)-2-hydroxy propyl] N'-methyl piperazinium malate,
(15) [3-(2,3-dihydroxy propylthio)-2-hydroxy propyl] diethylamine hydrochloride,
(16) [3-(2,2-dimethoxy ethylthio)-2-hydroxy propyl] dimethylamine hydrochloride,
(17) 4-[3-(3,3-dimethoxy propylthio)-2-hydroxy propyl] morpholine,
(18) [2-hydroxy-3-(2-pyridyl thio) propyl] dimethylamine dihydrochloride,
(19) [2-hydroxy-3(2-pyridyl ethylthio) propyl] diethylamine dihydrochloride,
(20) 1-[2-hydroxy-3-(2-pyridyl thio) propyl] pyrrolidine dihydrochloride,
(21) N-(3-benzylthio-2-hydroxy propyl) N'-phenyl piperazinium tartrate,
(22) (3-benzylthio-2-hydroxy propyl) diisopropylamine hydrochloride,
(23) N-(3-benzylthio-2-hydroxy propyl) morpholine hydrochloride,
(24) N-(3-benzylthio-2-hydroxy propyl) pyrrolidinium glutamate,
(25) (3-benzylthio-2-hydroxy propyl) bis (2-hydroxy ethyl) amine hydrochloride,
(26) N-(3-benzylthio-2-hydroxy propyl) piperidine hydrochloride,
(27) (3-benzylthio-2-hydroxy propyl) diethylamine hydrochloride,
(28) (3-decylthio-2-hydroxy propyl) methylbenzylamine hydrochloride,
(29) (3-p-chlorobenzylthio-2-hydroxy propyl) diethylamine hydrochloride,
(30) N-(3-o-chlorobenzylthio-2-hydroxy propyl) pyrrolidine hydrochloride,
(31) 4-(3-o-fluorophenylthio-2-hydroxy propyl) morpholine,
(32) 1-(3-o-chlorobenzylthio-2-hydroxy propyl) piperidine,
(33) 1-(3-p-fluorobenzylthio-2-hydroxy propyl) 4-methyl piperazine,
(34) (3-m-fluorobenzylthio-2-hydroxy propyl) dimethylamine hydrochloride,
(35) (3-p-bromophenylthio-2-hydroxy propyl) diethylamine hydrochloride,
(36) N-[3-(3,4-dichloro benzylthio)-2-hydroxy propyl] piperidine,
(37) [2-hydroxy-3-(p-methoxybenzylthio) propyl] diisopropylamine hydrobromide,
(38) [3-(p-butoxybenzylthio)-2-hydroxy propyl] bis (2-hydroxy ethyl) amine,
(39) N-[3-(3,4-dimethoxy benzylthio)-2-hydroxy propyl] piperidine hydrochloride,
(40) (2-hydroxy-3-phenylthio propyl) dicyclohexylamine,
(41) (2-hydroxy-3-phenylthio propyl) bis (2-hydroxy ethyl) amine hydrochloride,
(42) N-(3-p-aminophenylthio-2-hydroxy propyl) pyrrolidine,
(43) N-(3-p-dimethylaminophenylthio-2-hydroxy propyl) piperidine,
(44) N-(2-hydroxy-3-piperonylthio propyl) morpholine hydrochloride,
(45) (3-o-aminophenylthio-2-hydroxy propyl) diethylamine,
(46) N-[3-o-aminophenylthio-2-hydroxy propyl] morpholine hydrochloride,
(47) N-(3-benzhydrylthio-2-hydroxy propyl) morpholine,
(48) (2-hydroxy-3-$\alpha$-phenethylthio propyl) diethylamine,
(49) 3-(2-hydroxy-3-morpholino propylthio) alanine,
(50) N-(3-$\beta$-aminoethylthio-2-hydroxy propyl)N'-phenyl piperazine,
(51) [2-hydroxy-3-(2-chlorobenzamido ethylthio) propyl] diethylamine,
(52) N-[2-hydroxy-3-(2-nicotinamido ethylthio) propyl] piperidine,
(53) N-[2-hydroxy-3-(2-dodecanamido ethylthio) propyl] piperidine hydrochloride,
(54) N-[2-hydroxy-3-(2-o-methoxybenzamido ethylthio) propyl] piperidine,
(55) N-[2-hydroxy-3-(2-phenylacetamido ethylthio) propyl] piperidine,

(56) N-[2-hydroxy-3-(10-undecene-2-amido ethylthio) propyl] morpholine,
(57) 5-hydroxy-6-piperidino-3-thia hexanoic acid,
(58) 5-hydroxy-6-pyrrolidino-3-thia hexanoic acid,
(59) 5-hydroxy-6-morpholino-3-thia hexanoic acid,
(60) 11-(2-hydroxy-3-morpholino propylthio) undecanoic acid,
(61) 5-hydroxy bis-6-(hydroxyethylamino)-3-thia hexanoic acid,
(62) 5-hydroxy-6-(4-methyl piperazino)-3-thia hexanoic acid,
(63) 3-(2-hydroxy-3-piperidino propylthio) propanoic acid,
(64) 5-hydroxy-6-(N-methylbenzylamino)-3-thia hexanoic acid,
(65) 6-dicyclohexylamino-5-hydroxy-3-thia hexanoic acid,
(66) 6-diethylamino-5-hydroxy-3-thia hexanoic acid,
(67) N-(3-decylthio-2-hydroxy propyl) piperidine hydrochloride,
(68) N-(2-hydroxy-3-octylthio propyl) piperidine hydrochloride,
(69) N-(2-hydroxy-3-octadecylthio propyl) piperidine hydrochloride,
(70) N-(2-hydroxy-3-phenylthio propyl) N'-methyl piperazine dihydrochloride,
(71) N-(3-benzylthio-2-hydroxy propyl) N'-methyl piperazine dihydrochloride and
(72) N-(2-hydroxy-3-β-hydroxyethylthio propyl) piperidine hydrochloride.

METHODS OF PREPARATION

The compounds of the present invention can be prepared according to three reaction schemes (a), (b) and (c) as follows:

Reaction Scheme (a)

R—SH + X—CH$_2$—CH(OH)—CH$_2$—NR$_1$R$_2$  →

(I)  (II)

R—S—CH$_2$—CH(OH)—CH$_2$—NR$_1$R$_2$ + HX (III)

wherein X = Hal, —OSO$_2$CH$_3$ or —OSO$_2$C$_6$H$_4$pCH$_3$.

Reaction Scheme (b)

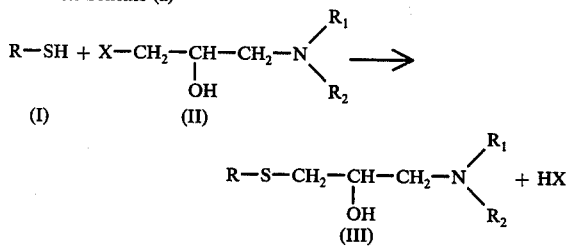

(I)  (IV)

R—S—CH$_2$—CH(OH)—CH$_2$—NR$_1$R$_2$ + HX (III)

wherein X has the meanings given above.

Reaction Scheme (c)

RX + HS—CH$_2$—CH(OH)—CH$_2$—NR$_1$R$_2$  →

(V)  (VI)

R—S—CH$_2$—CH(OH)—CH$_2$—NR$_1$R$_2$ + HX (III)

wherein X has the meanings given above.

As can be seen, reactions (a) and (b) are effected in both cases by beginning with a thiol R-SH(I) which is reacted either on a halogenide or on a 3-amino-2-hydroxy propyl sulfonate (II), or on a 3-hydroxy azetidinium salt (IV). The halogenides or 3-amino-2-hydroxy propyl sulfonates are obtained by the addition of a secondary amine of the type R$_1$R$_2$NH on epichlorohydrin or on a glycidyl sulfonate. Because of the instability of these halogenides or 3-amino-2-hydroxy propyl sulfonates, which can rather easily be transformed into an azetidinium (IV), particularly under the action of heat and in the course of time, it is preferable not to isolate them but rather react them directly with the thiol, R-SH (I).

On the other hand, the 3-hydroxy azetidinium salts (IV) are stable and can be isolated and optionally purified. These azetidinium salts can, for example, be prepared in accordance with German Pat. No. 1,111,638.

Reaction scheme (C) reverses the reaction partners in the sense that the radical R is linked to the halogen or to the sulfonate function while the 3-amino-2-hydroxy propyl radical carries the thiol function.

Compounds (VI) and (I) can be replaced by a precursor such as an isothiouronium salt of formula (VII) or (VIII), given below which is capable of liberating compound (VI) or (I) in the reaction medium by the action of a base of the same type as those which permit the reactions (c) and (a).

Compound (VII):

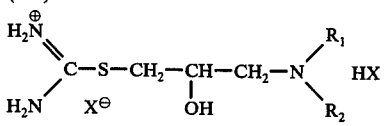

Compound (VIII)

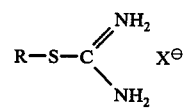

Generally, reaction schemes (a), (b) and (c) are effected under conventional conditions required for nucleophilic substitution; thus, the solvent can be water, alcohol, dioxane or dimethyl formamide, alone or in admixture. The base employed can be either an alkali or alkaline earth hydroxide or carbonate or an alkali or alkaline earth alcoholate or hydride, or it can be ammonia or even an aliphatic tertiary amine, such as triethylamine.

Reactions (a), (b) and (c) are generally carried out at a temperature between 30°–100° C, the reaction time often being about 30 minutes to 10 hours.

To obtain the active compounds in salt form, the acid corresponding to the desired salt, is first dissolved in an appropriate solvent. Then there is introduced into this solution, the active compound either in the pure state or in the dissolved state, preferably in the same solvent which serves for the dissolution of the acid. The solvent selected, preferably is not a solvent for the desired salt.

To prepare the hydrochlorides, it is generally more advantageous to dissolve the active compound in an appropriate solvent, after which gaseous HCl is bubbled therethrough. The hydrochloride of the desired compound generally precipitates under these conditions.

In order to better understand the invention the following non-limiting examples are given which relate to the preparation of the active compounds as well as to compositions containing the same.

EXAMPLES OF PREPARATION

Example 1

Preparation of (3-benzylthio-2-hydroxy propyl) diethylamine hydrochloride.

6.20 g of benzylmercaptan and 2 g of NaOH are stirred together in 25 cc of water, under a nitrogen atmosphere, for 5 minutes at which time there is added thereto a solution of 8.28 g of 1,1-diethyl-3-hydroxy azetidinium chloride in 25 cc of ethyl alcohol. The resulting mixture is heated for 1 hour at 75° C. After evaporating to dryness the product thus obtained is taken up in ether. The resulting etherified solution is then dried on sodium sulfate and neutralized by bubbling gaseous HCl therethrough. The precipitate which forms is filtered and recrystallized in a mixture of ethyl acetate and ethanol, yielding 12.24 g of white crystals melting at 104° C.

Analysis: $C_{14}H_{24}NOS$ Cl: Calculated, %: C—58.03 H — 8.29 N— 4.84 S — 11.05: Found, %: C—57.96 H — 8.12 N— 4.67 S — 11.17.

Example 2

Preparation of 1-(3-benzylthio-2-hydroxy propyl) piperidine hydrochloride.

A mixture of 111.6 g of benzylmercaptan, 36 g of NaOH and 160 g of 2-hydroxy-4-azonia-[3,5] spiro nanone chloride in 500 cc of water is heated under a nitrogen atmosphere for 2 hours at 65° C. After cooling, the reaction mixture is extracted three times with chloroform. The resulting chloroform extract is then treated with 75 cc of 12N HCl diluted to 200 cc. The resulting aqueous phase is then evaporated to dryness and the solid residue obtained is crystallized in absolute ethanol, yielding 226 g of white crystals melting at 142° C.

Analysis: $C_{15}H_{24}NOSCl$: Calculated,%: C — 59.70 H — 7.96 N — 4.64 S — 10.62: Found, %: C — 59.71 H — 7.69 N — 4.48 S — 10.85.

Example 3

Preparation of N-(3-benzylthio-2-hydroxy propyl) morpholine.

12.40g (0.1 mol) of benzylmercaptan are mixed with 5.6g (0.1 mol) of KOH in 60 cc of water under a nitrogen atmosphere. To the resulting mixture there are added 18 g (0.1 mol) of 3'-hydroxy-4-morpholine-1'-spiro azetidinium chloride in 80cc of water. After 4 hours of heating at 70°-80° C, the mixture is cooled and extracted with chloroform. The chloroform phase is then treated with 120cc of normal HCl and the resulting aqueous phase thus obtained is evaporated to dryness.

The residue (29.6g) is then crystallized in 120cc of isopropanol, yielding 27.4g of white crystals melting at 115° C.

Analysis: $C_{14}H_{22}NO_2S$ Cl: Calculated, %: C — 55.35 H — 7.25 N — 4.61 S — 10.54: Found, %: C — 55.46 H — 7.08 N — 4.44 S — 10.73.

Example 4

Preparation of N-(3-benzylthio-2-hydroxy propyl) bis (2-hydroxy ethyl) amine.

A solution of 10.5g of diethanolamine in 15cc of ethanol is poured into a solution of 9.25g of epichlorohydrin in 10cc of ethanol while maintaining the temperature below 25° C. The resulting mixture, after 12 hours of agitation at ambient temperature is heated for 3 hours at reflux at which time it is evaporated under a vacuum and then taken up in acetone to yield 18.5g of white solid. 9.9g of this product in solution in 30 cc of ethanol were poured, under a nitrogen atmosphere, into 70cc of an ethyl alcohol solution obtained by the addition of 6.1g thereto of benzylmercaptan to 3.4 g of sodium ethylate. After agitating the resulting mixture for 1 hour at ambient temperature and 1 hour at reflux, the same is cooled. The sodium chloride formed is then filtered off. The resulting filtrate is treated with 7cc of concentrated HCl diluted to 50cc. The mixture is then evaporated to dryness and the residue is crystallized in 80cc of ethanol, yielding 11.2g of crystallized product in the form of needles having a melting point of 98° C.

Analysis: $C_{14}H_{24}NClO_3S$: Calculated, %: C — 52.25 H — 7.47 N — 4.35 S — 9.95: Found, %: C — 52.19 H — 7.32 N — 4.12 S — 10.04.

Example 5

Preparation of 5-hydroxy-6-piperidino-3-thia hexanoic acid.

To a solution of 9.2g of thioglycolic acid (0.1 mol) and 8g of NaOH (0.2 mol) in 60 cc of water, there is added over a 15 minute period under a nitrogen atmosphere a solution of 17.75g of 3'-hydroxy-1-piperidine-1'-spiro azetidinium chloride in 50cc of water. The resulting mixture is heated for 2 hours at 75° C at which time the reaction mixture is neutralized by the addition thereto of 100cc and then evaporated to dryness. The residue is taken up in 250 cc of absolute ethyl alcohol and the insoluble mineral salts are filtered therefrom. The resulting filtrate is left to stand for 12 hours at 5° C and then filtered thus yielding 16.75g of white crystals having a melting point of 152° C.

Analysis: $C_{10}H_{19}NO_3S$: Calculated, %: C — 51.50 H — 8.15 N — 6.01 S — 13.73: Found, %: C — 51.20 H — 8.19 N — 5.84 S — 13.57.

Example 6

Preparation of 6-diethylamino-5-hydroxy-3-thia hexanoic acid.

Into a solution of 18.4g of thioglycolic acid in 50cc of water neutralized by 16g of NaOH in 60cc of water, there is poured a solution of 33.1g of 1,1-diethyl-3-hydroxy azetidinium chloride in 90cc of water. The resulting mixture is heated for 5 hours at 70° C under a nitrogen atmosphere, at which time it is then neutralized by the addition thereto of 16.5cc of 12N HCl. The water is then expelled by distilling the reaction mixture under a vacuum and the residue is then taken up in 200cc of isopropanol. After eliminating the sodium chloride precipitate by filtration, the resulting alcoholic filtrate is evaporated to dryness. The residue is then taken up in 100cc of water and filtered through a bed of DOWEX50W resin in order to eliminate residual traces of sodium chloride. The thus treated aqueous solution is then evaporated to dryness yielding an oil which when treated with acetone provides 29.2g of a whitish product melting at 104° C.

Analysis: $C_9H_{19}NO_3S$: Calculated, %: C — 48.87 H — 8.60 N — 6.33 S — 14.48: Found,%: C — 48.52 H — 8.35 N — 6.22 S — 14.21.

Example 7

Preparation of 5-hydroxy-6-morpholino-3-thia hexanoic acid.

To an aqueous solution of 15.18g of thioglycolic acid there are added 18.5g of KOH. To the resulting mixture there is added over a 20 minute period an aqueous solution of 2.93g of 3'-hydroxy-4-morpholino-1'-spiro azetidinium chloride and the whole is then heated for 4 hours at 70° C on a water-bath. Thereafter, the reaction mixture is cooled, neutralized by the addition thereto of 13.75cc of 12N HCl and evaporated to dryness. The residue is taken up in dimethylformamide to remove the KCl. The resulting filtrate on cooling yields 34.71g of white crystals which on recrystallization in ethyl alcohol (90° titer) exhibit a melting point of 138° C, and an amine index of 4.23 meq/g for a theoretical 4.26 meq/g.

Analysis: $C_9H_{17}NO_4S$: Calculated, %: C — 45.94 H — 7.28 N — 5.95 S — 13.63: Found, %: C — 45.95 H — 7.38 N — 6.06 S — 13.58.

Example 8

Preparation of 5-hydroxy-bis 6-(hydroxyethylamino)-3-thia hexanoic acid.

Into a solution of 18.5g of epichlorohydrin in 20cc of ethanol, there are poured 21g of diethanolamine in solution in 30 cc of ethyl alcohol while maintaining the temperature below 25° C. After agitating the resulting mixture for 12 hours at ambient temperature, the same is heated to reflux and then evaporated under a vacuum to provide 37g of colorless oil.

This colorless oil is then dissolved in 50cc of water and poured into an aqueous solution of 18.4 g of thioglycolic acid previously neutralized with 22.4g of KOH. The resulting clear solution is maintained at 75° C for 2.5 hours, then neutralized by the addition thereto of 165cc of 12N HCl. The resulting solution is evaporated to dryness and the residue taken up in dimethyl formamide at 100° C. After filtering the KCl therefrom, the filtrate yields on cooling 35.5g of lightly colored product which on recrystallization in ethyl alcohol (90° titer) yields 30.5g of white crystals metling at 148° C.

Analysis: $C_9H_{19}NO_5S$: Calculated, %: C — 42.69 H — 7.51 N — 5.53 S — 12.65: Found, %: C — 42.92 H — 7.13 N — 5.24 S — 12.59.

Example 9

Preparation of 3-(2-hydroxy-3-morpholino propylthio) alanine.

Into an aqueous solution of 17.55g of monohydrated cysteine hydrochloride there is introduced, under a nitrogen atmosphere, a solution of 8g of NaOH in 35cc of water. To the resulting solution there is then added a solution of 17.95g of 3'-hydroxy-4-morpholino-1'-spiro azetidinium chloride in 40cc of water. After heating this reaction mixture for 2 hours at 65° C, the solution diluted by a quantity of water half its volume is filtered on DOWEX 50W resin to remove the mineral salts. The filtrate is then evaporated to dryness and the residue recrystallized in ethyl alcohol (85° titer), yielding 18.45g of a white product melting at 200° C with decomposition and having an amine index of 7.55 meq/g for a theoretical 7.57 meq/g.

Analysis: $C_{10}H_{20}N_2O_4S$: Calculated,%: C — 45.45 H — 7.58 N — 10.61 S — 12.12: Found,%: C — 45.63 H — 7.31 N — 10.75 S — 12.03.

Example 10

Preparation of N-(2-hydroxy-3-phenylthio propyl) bis (2-hydroxy ethyl) amine hydrochloride.

Into a solution of 5.55 g of epichlorohydrin in 10cc of ethanol there are poured 6.3g of diethanolamine dissolved in 15cc of ethanol while maintaining the temperature below 25° C. After agitating the resulting mixture for 12 hours at ambient temperature the same is heated at reflux for 3 hours and then evaporated to dryness. The residue is then pulverized in the presence of acetone, yielding 11.85g of a white solid.

This white solid, dissolved in 25cc of methanol, is then poured into a solution of 6.6g of thiophenol in 20cc of methanol. To this solution there is then added a solution of 3.36g of KOH in 30cc of methanol. The resulting reaction mixture is then heated at reflux for 4 hours at which time the solvent is evaporated therefrom under a vacuum and the residue taken up in 70cc of chloroform. More KCl is filtered therefrom and the filtrate is neutralized by the addition thereto of 60cc of normal HCl.

The aqueous phase is then evaporated to dryness and after recrystallizing the residue in isopropanol, there are obtained 11.23g of white crystals melting at 116° C.

Analysis: Calculated, %: C - 50.73 H - 7.15 N - 4.55 S - 10.41: Found,%: C - 50.58 H - 7.40 N - 4.60 S - 10.61.

Example 11

Preparation of 1-(2-hydroxy-3-phenylthio propyl) piperidine hydrochloride.

To a solution of 188g of potassium thiophenate in 500cc of water, there is added a solution of 226g of 2-hydroxy-4-azonia [3,5]spiro nonane chloride in 500cc of water. The resulting mixture is then heated for 5.5 hours at 75° C, at which time the same is cooled to ambient temperature and extracted 3 times with 150cc of chloroform. The chloroform extract is then neutralized with 102cc of concentrated HCl, diluted 4 times. The resulting aqueous phase is evaporated to dryness yielding 327g of a white solid which is recrystallized in 700cc of isopropanol, yielding 317g of white crystals melting at 134° C. Proportion of "ionized chloride": 3.47 meg/g for a theoretical 3.48 meg/g.

Analysis: $C_{14}H_{22}NOSCl$: Calculated, %: C - 58.43 H - 7.65 N - 4.87 S - 11.13: Found, %: C - 58.26 H - 7.85 N - 4.81 S - 11.16.

Example 12

Preparation of 1-(2-hydroxy-3-phenylthio propyl) morpholine hydrochloride.

Example 11 is repeated except that sodium thiophenate is used instead of potassium thiophenate and the 2-hydroxy-4-azonia [3.5] spiro nonane chloride is replaced by 3'-hydroxy-4-morpholine-1'-spiro azetidinium chloride, to provide white crystals melting at 132° C.

Analysis: $C_{13}H_{20}ClNO_2S$: Calculated, %: C - 53.89 H - 6.92 N - 4.83 S - 11.05: Found, %: C - 54.06 H - 7.03 N - 4.79 S - 10.90.

Example 13

Preparation of N-(3-dodecylthio-2-hydroxy propyl) piperidine hydrochloride.

A solution of 0.1 mol. of sodium dodecylthiolate in ethanol is prepared by adding 0.1 mole of 1-dodecane thiol to a normal solution of sodium ethylate in ethanol. To this sodium dodecylthiolate solution there are added, little by little, 17.75g of 2-hydroxy-4-azonia-[3,5] spiro nonane chloride in 35 ml of ethanol. The mixture is heated for 5 hours on a water-bath and then filtered. The resulting filtrate is saturated with dry gaseous HCl and cooled. The resulting precipitate which forms (13.8g) is then filtered and washed with acetone and exhibits a melting point of 102° C.

Analysis: $C_{20}H_{42}ClNOS$: Calculated,%: C - 63.24 H - 11.07 N - 3.69 S - 8.43: Found, %: C - 63.03 H - 11.10 N - 3.68 S - 8.51.

Example 14

Preparation of N-(2-hydroxy-3-octylthio propyl) piperidine hydrochloride.

Example 13 is repeated except that the 1-dodecane thiol is replaced by 1-octane thiol, to yield white crystals exhibiting a melting point of 88° C.

Analysis: $C_{16}H_{34}ClNOS$: Calculated,%: C - 59.35 H - 10.51 N - 4.33 S - 9.80: Found, %: C - 59.60 H - 10.25 N - 4.04 S - 9.93.

Example 15

Preparation of N-(3-decylthio-2-hydroxy-propyl) piperidine hydrochloride.

Example 13 is repeated except that the 1-dodecane thiol is replaced by 1-decane thiol, to yield white crystals melting at 95° C.

Analysis: $C_{18}H_{38}ClNOS$: Calculated, %: C - 61.45 H - 10.81 N - 3.98 S - 9.10: Found, %: C - 61.43 H - 10.66 N - 3.89 S - 9.16.

Example 16

Preparation of N-[2-hydroxy-3-octadecylthio propyl] piperidine hydrochloride.

Example 13 is repeated except that the 1-dodecane thiol is replaced by octadecane thiol to yield white crystals melting at 97° C.

Analysis: $C_{26}H_{54}ClNOS$: Calculated, %: C - 67.31 H - 11.65 N - 3.02 S - 6.90: Found, %: C - 67.02 H - 11.79 N - 2.93 S - 7.07.

Example 17

Preparation of N-(2-hydroxy-3 phenylthio propyl) N'-methyl piperazine dihydrochloride.

Example 12 is repeated except that the 3'-hydroxy-4-morpholin-1'-spiro azetidinium chloride is replaced by 3'-hydroxy-4-methyl-1-piperazine-1'-spiro azetidinium chloride to provide white crystals melting at 205° C.

Analysis: $C_{14}H_{24}Cl_2N_2OS$: Calculated, %: C - 49.56 H - 7.08 N - 8.26 S - 9.44: Found, %: C - 49.74 H - 6.82 N - 8.19 S - 9.39.

Example 18

Preparation of N-(2-hydroxy-3-β-hydroxyethylthio propyl) piperidine hydrochloride.

Example 2 is repeated except that the benzylmercaptan is replaced by mercapto ethanol to yield white crystals melting at 66° C.

Analysis: $C_{10}H_{22}ClNO_2S$: Calculated, %: C - 46.96 H - 8.61 N - 5.48 S - 12.52: Found, %: C - 46.56 H - 8.58 N - 5.71 S - 12.42.

Example 19

Preparation of N-(3-benzylthio-2-hydroxy propyl) pyrrolidine hydrochloride.

Example 2 is repeated except that the 2-hydroxy-4-azonia -[3,5] - spiro nonane chloride is replaced by 4-azonia-2-hydroxy-[3,4] spiro octane chloride to yield white crystals melting at 103° C.

Analysis: $C_{14}H_{22}ClNOS$: Calculated, %: C - 58.36 H - 7.65 N - 4.87 S - 11.12: Found, %: C - 58.32 H - 7.45 N - 4.87 S - 10.92.

Example 20

Preparation of N-(2-hydroxy-3-phenylthio propyl) dicyclohexylamine hydrochloride.

One mol of thiphenol is dissolved in a solution of 46 g of sodium of ethanol. To the resulting solution there is progressively added 1 mol of an ethanolic solution of (3-chloro-2-hydroxy propyl) dicyclohexylamine hydrochloride. This mixture is then heated for two hours at reflux. After cooling the same, the reaction mixture is filtered and the filtrate evaporated to dryness. The resulting oily residue is taken up in sulfuric ether, through which there is then bubbled gaseous HCl. A white precipitate rapidly forms which is then filtered therefrom and recrystallized in ethanol for a 63 percent yield of white crystals melting at 181° C.

Analysis: $C_{21}H_{34}ClNOS$: Calculated, %: C - 65.71 H - 8.87 N - 3.65 S - 8.34: Found, %: C - 65.73 H - 8.86 N - 3.36 S - 8.37.

Examples of Compositions

Example 21

A liquid shampoo composition is prepared by admixing the following components:

| | |
|---|---|
| Triethanolamine lauryl sulfate | 4g |
| Lauryl diethanolamide | 2g |
| 1-(3-benzylthio-2-hydroxy propyl) diethylamine hydrochloride | 1g |
| Carboxymethyl cellulose | 0.2g |
| Perfume (phenyl alcohol, benzyl acetate, etc.) | 0.3g |
| Water, q.s.p. | 100g |

Example 22

A liquid shampoo composition is prepared by admixing the following components:

| | |
|---|---|
| Sodium lauryl sulfate oxyethylenated with 2.2 mols of ethylene oxide | 5g |
| Sodium mono lauryl sulfosuccinate | 1g |
| Polyethylene glycol distearate | 1.5g |
| Lauryl diethanolamide | 2.5g |
| 1-(3-benzylthio-2-hydroxy propyl) piperidine hydrochloride | 2g |
| Perfume (essence of rose) | 0.3g |
| Lactic acid, q.s.p. | pH 6.5 |
| Water, q.s.p. | 100g |

Example 23

A composition in accordance with the invention for combatting the greasy and unaesthetic appearance of the hair and skin is prepared by admixing the following components:

| | |
|---|---|
| 1-N-(3-benzylthio-2-hydroxy propyl) morpholine | 1.5g |
| Perfumed distilled water | 100 cc |

Example 24

A composition for combatting the greasy and unaesthetic appearance of the hair and skin is prepared by admixing the following components:

| | |
|---|---|
| N-(3-benzylthio-2-hydroxy propyl)bis (2-hydroxy ethyl)amine hydrochloride | 2 g |
| 20% aqueous ethanol solution | 100 cc |

Example 25

A solution for treating the scalp is prepared by admixing the following components:

| | |
|---|---|
| 5-hydroxy-6-piperidino-3-thia hexanoic acid | 0.75 g |
| Dimethyl hydantoin formaldehyde resin | 0.5 g |
| Dimethyl dilauryl ammonium chloride | 0.5 g |
| Perfume | 0.1 g |
| Ethanol | 50 cc |
| Water, q.s.p. | 100 g |

Example 26

A liquid gel for treating the scalp is prepared by admixing the following components:

| | |
|---|---|
| 6-diethylamino-5-hydroxy-3-thia hexanoic acid | 0.1 g |
| Carboxypolymethylene-a carboxyvinyl polymer sold under the trade name Carbopol 940 | 0.45 g |
| Polyvinylpyrrolidone (MW=40,000) | 2 g |
| Lanolin oxyethylenated with 16 mols of ethylene oxide | 1 g |
| Polyethylene glycol (MW=300) | 5 g |
| Methyl p-hydroxybenzoate | 0.1 g |
| Propyl p-hydroxybenzoate | 0.1 g |
| Perfume | 0.1 g |
| Triethanolamine, q.s.p. | pH 8 |
| Water, q.s.p. | 100 g |

Example 27

A face cream is prepared by admixing the following components:

| | |
|---|---|
| 5-hydroxy-6-morpholino-3-thia hexanoic acid | 2 g |
| Cetylstearyl alcohol oxyethylenated with 15 mols of ethylene oxide | 7 g |
| Silicone oil (dimethyl polysiloxane having a viscosity of 20–22° at ambient temperature) | 1 g |
| Diethylene glycol stearate | 6 g |
| Methyl p-hydroxybenzoate | 0.1 g |
| Propyl p-hydroxybenzoate | 0.1 g |
| Water, q.s.p. | 100 g |

Example 28

A cosmetic milk formulation is prepared by admixing the following components:

| | |
|---|---|
| 3-(2-hydroxy-3-morpholino propylthio) alanine | 3 g |
| Carboxypolymethylene-a carboxyvinyl polymer sold under the trade name Carbopol 934 | 0.375 g |
| Isopropyl esters of fatty acids of lanolin | 1 g |
| Lanolin oxyethylenated with 16 mols of ethylene oxide | 2.5 g |
| Cetylstearyl alcohol oxyethylenated with 15 mols of ethylene oxide | 3 g |
| Substituted alkylamide | 2 g |
| Ethyl alcohol | 20 cc |
| Triethanolamine, q.s.p. | pH=8 |
| Methyl p-hydroxybenzoate | 0.1 g |
| Propyl p-hydroxybenzoate | 0.1 g |
| Water, q.s.p. | 100 g |

EXAMPLE 29

A skin defect concealing cream is prepared by admixing the following components:

| | |
|---|---|
| N-[3-(2-dimethylamino ethylthio)-2-hydroxy propyl] diethylamine dihydrochloride | 5 g |
| Titanium oxide | 10 g |
| Red iron oxide | 0.3 g |
| Yellow iron oxide | 0.4 g |
| Maroon iron oxide | 0.4 g |
| Brown iron oxide | 0.2 g |
| Cetylstearyl alcohol oxyethylenated with 15 mols ethylene oxide | 7 g |
| Silicone oil (dimethylpolysiloxane having a viscosity of 20–22 at ambient temperature) | 1gg |
| Polyglycol monostearate (MW of the polyglycol=400) | 6 g |
| Methyl and propyl esters of p-hydroxybenzoate | 0.2 g |
| Water, q.s.p. | 100 g |

EXAMPLE 30

A lotion is prepared by admixing the following components:

| | |
|---|---|
| N-(2-hydroxy-3-phenylthio propyl)bis (2-hydroxy ethyl)amine hydrochloride | 0.25 g |
| N-(3-dodecylthio-2-hydroxy propyl) piperidine hydrochloride | 0.75 g |
| Perfume | 0.05 g |
| Ethanol solution (96° titer) | 20.8 g |
| Water, q.s.p. | 100 g |

EXAMPLE 31

A colored hair setting lotion for application to white hair having a greasy appearance is prepared by admixing the following components:

| | |
|---|---|
| Polyvinylpyrrolidone (MW=40,000) | 0.4 g |
| Vinylacetate/crotonic acid copolymer, 90:10, MW=20,000 | 0.2 g |
| Ethanol, q.s.p. 50° | |
| N-(3-octylthio-2-hydroxy propyl) piperidine hydrochloride | 0.7 g |
| 1-aminopropyl aminoanthraquinone | 0.03 g |
| Picramic acid | 0.17 g |
| 4-N-α-aminopropylamino-1-N'-methyl aminoanthraquinone | 0.04 g |
| Water, q.s.p. | 100 g |
| Triethanolamine, q.s.p. | pH 7 |

The above hair setting lotion when applied to white hair imparts thereto a smoke gray coloration and improves the greasy appearance of the hair.

EXAMPLE 32

A shampoo composition is prepared by admixing the following components:

| | |
|---|---|
| Lauryl sulfate triethanolamine | 5 g |
| Lauryl diethanolamide | 2 g |

| | |
|---|---|
| N-(3-decylthio-2-hydroxy propyl) piperidine hydrochloride | 2 g |
| Carboxymethyl cellulose | 0.25 g |
| Perfume | 0.2 g |
| Water, q.s.p. | 100 g |

EXAMPLE 33

A shampoo composition in powder form is prepared by admixing the following components:

| | |
|---|---|
| Sodium lauryl sulfate (powder) | 50 g |
| Condensation product of fatty acids of copra with sodium isethionate, sold under the trade name "Hostapon K.A" | 41 g |
| 1-(2-hydroxy-3-phenylthio propyl) morpholine hydrochloride | 8 g |
| Perfume | 1 g |

EXAMPLE 34

A shampoo composition in powder form is prepared by admixing the following components:

| | |
|---|---|
| Sodium lauryl sulfate (powder) | 40 g |
| 1-(2-hydroxy-3-phenylthio propyl) piperidine hydrochloride | 20 g |
| "Hostapon K.A" (as in Example 33) | 29 g |
| Perfume | 1 g |

The powdered shampoo compositions of Examples 33 and 34 can be dissolved in 10 times their weight of water and the resulting solution applied to the hair to improve the greasy and unaesthetic appearance thereof.

EXAMPLE 35

A shampoo dye composition is prepared by admixing the following components:

| | |
|---|---|
| 5-hydroxy bis-6-(hydroxy ethylamino)3-thia hexanoic acid | 5 g |
| Ammonium lauryl sulfate oxyethylenated with 2 mols ethylene oxide | 250 g |
| Copra diethanolamide | 50 g |
| Paratoluene diamine | 10 g |
| Methanediamino anisol sulfate | 0.5 g |
| Resorcinol | 5 g |
| Meta-aminophenol | 1.5 g |
| Para-aminophenol | 1 g |
| Ethylene diamine tetraacetic acid | 3 g |
| Sodium bisulfite (40%) | 15 g |
| Water, q.s.p. | 1000 g |

The above resulting mixture is then admixed with 1000g of $H_2O_2$ (20 volumes), the same then being used to impregnate 85% white hair to impart thereto a chestnut coloration and to essentially eliminate any greasy appearance of the hair. The above shampoo composition has a pH between 6.5-8.

EXAMPLE 36

The first stage (reducing stage) of a permanent waving operation is carried out in a conventional manner using the following reducing composition:

| | |
|---|---|
| Ammonium thioglycolate | 9.5 g |
| Polyethoxyester of fatty alcohol (30% cetyl alcohol - 70% stearyl alcohol, sold under the trade name "Cire de Cipol A.O." | 0.8 g |
| Ammonium solution, q.s.p. 0.7N | |
| Water, q.s.p. | 100 g |

In the second stage (a neutralization stage) the following composition, packaged in two parts, is utilized:

| | |
|---|---|
| 1st part | |
| $H_2O_2$, q.s.p. | 6.6 volumes |
| Citric acid | 0.1 g |
| Water, q.s.p. | 100 g |
| 2nd part | |
| N-(3-benzylthio-2-hydroxy propyl) bis (2-hydroxy ethyl)amine hydrochloride | 1.5 g |

Immediately before carrying out the second stage of the permanent waving operation, i.e. before the neutralization stage, the N-(3-benzylthio-2-hydroxy propyl)-bis-(2-hydroxy ethyl)amine hydrochloride, in the form of a powder, is dissolved in the $H_2O_2$ solution of the 1st part defined above. The resulting mixture is then applied to the hair which had previously been reduced and rolled upon curlers for a time sufficient to reform the disulfide links of the keratin of the hair.

After having rinsed the hair, removed the rollers and dried the hair, there is thus obtained a permanent wave exhibiting very good holding characteristics. Further the thus treated hair has a very good non-greasy appearance.

EXAMPLE 37

An orally administrable composition for combatting against a greasy and unaesthetic appearance of the skin and hair is prepared by admixing the following components:

| | |
|---|---|
| 6-diethylamino-5-hydroxy-3-thia hexanoic acid | 50 mg |
| Glucose | 300 mg |
| Water, q.s.p. | 5 ml |
| Orange juice, q.s.p. to aromatize the composition. | |

The oral administration of this composition at the rate of two ampoules per day for 18 days to a person having greasy hair significantly improves the condition of the scalp and the appearance of the hair.

EXAMPLE 38

Chewable tablets having the following composition are prepared:

| | |
|---|---|
| N-(3-benzylthio-2-hydroxy propyl) morpholine hydrochloride | 5 g |
| Glucose | 200 g |
| Lemon syrup | 50 g |

These tablets administered at a rate of one coffee spoon twice a day for a period of about 15 days to a person having greasy hair significantly reduces the greasy appearance of the hair and improves the condition of the scalp.

EXAMPLE 39

Orally administrable tablets are prepared by admixing the following components:

| | |
|---|---|
| N-(3-octylthio-2-hydroxy propyl) piperidine hydrochloride | 10 mg |
| Lactose | 150 mg |
| Gum arabic | 100 mg |
| Starch, q.s.p. | 500 mg |

These tablets taken at a rate of 10 per day for a period of 20 days by a person having greasy hair improves the appearance of the hair and the condition of the scalp.

What is claimed is:

1. A cosmetic composition for combatting the greasy and unaesthetic appearance of the hair and to improve the appearance of the skin comprising a solvent selected from the group consisting of water, lower alkanol and an aqueous solution of said lower alkanol, and 0.1 to 20% by weight of an active compound selected from the group consisting of:

(1) a compound of the formula

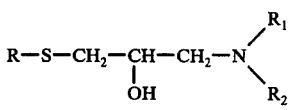

wherein $R_1$ and $R_2$ each independently are selected from the group consisting of methyl, ethyl, isopropyl, cyclohexyl, benzyl and $\beta$-hydroxyethyl, and R is selected from the group consisting of (i) linear or branched alkyl having 1–18 carbon atoms, (ii) alkenyl having 3–18 carbon atoms, (iii) alkyl having 2–3 carbon atoms and substituted by 1–2 alcohol functions, (iv) $-(CH_2)_m-CH(OR_3)_2$ wherein $R_3$ is alkyl having 1–4 carbon atoms and $m$ is 1–2, (v) $-(CH_2)_n R_4$ wherein $n$ is 0, 1 or 2 and $R_4$ is phenyl, (vi) $-(CH_2)_q R'_4$ wherein $q$ is 0 or 1 and $R'_4$ is

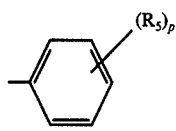

wherein $p$ is 1, 2 or 3 in which instance $R_5$ is selected from the group consisting of F, Cl, Br, alkoxy having 1–5 carbon atoms and alkyl having 1–4 carbon atoms or wherein $p$ is 1 in which instance $R_5$ is selected from the group consisting of amino and dimethylamino, (vii) $-CH_2-CH_2-NH-Y$ wherein Y is selected from the group consisting of hydrogen and $COR_9$ wherein $R_9$ is selected from the group consisting of hydrogen, alkyl having 1–18 carbon atoms and

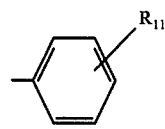

wherein $R_{11}$ is selected from the group consisting of H, F, Cl, Br and alkoxy having 1–4 carbon atoms, and (viii) $-(CH_2)_s-COOH$ wherein $s$ is 1–10, and (2) a salt of the compound in (1).

2. The composition of claim 1 wherein said active compound is present in the form of a salt of an acid selected from the group consisting of hydrochloric acid, hydrobromic acid, sulfuric acid, phosphoric acid, malic acid, citric acid, 3-hydroxy butyric acid, lactic acid, gluconic acid, isethionic acid, salicyclic acid, glutamic acid, aspartic acid, camphocarbonic acid, camphosulfonic acid, tartaric acid and nicotinic acid.

3. The composition of claim 1 wherein said active compound is selected from the group consisting of:

(1) (2-hydroxy-3-octadecylthio propyl) dimethylamine hydrochloride, (2) (3-hexadecylthio-2-hydroxy propyl) bis ($\beta$-hydroxyethyl) amine hydrochloride, (3) [2-hydroxy-3-(octadecene-9-ylthio)propyl] dicyclohexylamine hydrochloride, (4) [3-(butene-2-ylthio)-2-hydroxy propyl] diethylamine hydrochloride, (5) [3-(2,3-dihydroxy propylthio)-2-hydroxy propyl] diethylamine hydrochloride, (6) [3-(2,2-dimethoxy ethylthio)-2-hydroxy propyl] dimethylamine hydrochloride, (7) (3-benzylthio-2-hydroxy propyl) diisopropyl amine hydrochloride, (8) (3-benzylthio-2-hydroxy propyl) bis (2-hydroxy ethyl) amine hydrochloride, (9) (3-benzylthio-2-hydroxy propyl) diethylamine hydrochloride,

(10) (3-decylthio-2-hydroxy propyl) methyl benzylamine hydrochloride,

(11) (3-p-chlorobenzylthio-2-hydroxy propyl) diethylamine hydrochloride,

(12) (3-m-fluorobenzylthio-2-hydroxy propyl) dimethylamine hydrochloride,

(13) (3-p-bromophenylthio-2-hydroxy propyl) diethylamine hydrochloride,

(14) [3-(2,4-dichloro benzylthio)-2-hydroxy propyl] diethylamine,

(15) (2-hydroxy-3-p-methoxybenzylthio propyl) diisopropylamine hydrobromide,

(16) [3-(p-butoxy benzylthio)-2-hydroxy propyl] bis (2-hydroxy ethyl) amine,

(17) [2-hydroxy-3-(o-methylbenzylthio) propyl] diethylamine,

(18) (2-hydroxy-3-phenylthio propyl) dicyclohexylamine,

(19) (2-hydroxy-3-phenylthio propyl) bis (2-hydroxy ethyl) amine hydrochloride,

(20) (3-o-aminophenylthio-2-hydroxy propyl) diethylamine,

(21) (2-hydroxy-3-$\alpha$-phenetylthio propyl) diethylamine,

(22) [2-hydroxy-3-(2-chlorobenzamido ethylthio) propyl] diethylamine,

(23) 5-hydroxy bis-6-(hydroxyethylamino)-3-thia hexanoic acid,

(24) 5-hydroxy-6-(N-methylbenzylamino)-3-thia hexanoic acid,

(25) 6-dicyclohexylamino-5-hydroxy-3-thia hexanoic acid,

(26) 6-diethylamino-5-hydroxy-3-thia hexanoic acid,

(27) [2-hydroxy-3-(2-tetradecanamido ethylthio) propyl] diethylamine hydrochloride, and

(28) [2-hydroxy-3-(2-hexadecanamido ethylthio) propyl] diethylamine hydrochloride.

4. The composition of claim 3 wherein said active compound is 6-diethylamino-5-hydroxy-3-thia hexanoic acid.

5. The composition of claim 1 wherein said active compound is present in an amount of 0.5-10 percent by weight of said composition.

6. The composition of claim 1 wherein said carrier is selected from the group consisting of a lower alkanol and an aqueous solution of a lower alkanol, and which also includes a cosmetic film forming resin.

7. The composition of claim 1 which also includes a detergent selected from the group consisting of an anionic, a cationic, a nonionic and an amphoteric detergent.

8. The composition of claim 1 which also includes at least one reducing agent for the disulfide bonds of keratin.

9. The composition of claim 1 which also includes an oxidizing agent for reforming the disulfide bonds of keratin.

10. The composition of claim 1 which also contains a thiol and an organic disulfide, the molar ratio of said disulfide to said thiol being greater than 1.

11. The composition of claim 1 which also includes a bactericide or fungicide.

12. A process for combatting the greasy and unaesthetic appearance of the hair and to improve the appearance of the skin comprising applying to the hair and to skin so characterized an effective amount of the composition of claim 1.

* * * * *